(12) United States Patent
Hoffman et al.

(10) Patent No.: US 9,345,611 B2
(45) Date of Patent: May 24, 2016

(54) CERVICAL REPOSITIONING, RESTRAINT, TRACTION AND EXERCISE DEVICE AND METHOD

(75) Inventors: Swee Lin Hoffman, Sunnyvale, CA (US); Steven Ari Hoffman, Sunnyvale, CA (US)

(73) Assignee: Backproject Corporation, Sunnyvale, CA (US)

( * ) Notice: Subject to any disclaimer, the term of this patent is extended or adjusted under 35 U.S.C. 154(b) by 0 days.

(21) Appl. No.: 13/469,038

(22) Filed: May 10, 2012

(65) Prior Publication Data

US 2013/0131570 A1 May 23, 2013

Related U.S. Application Data

(60) Provisional application No. 61/484,802, filed on May 11, 2011.

(51) Int. Cl.
  *A61F 5/00* (2006.01)
  *A61F 5/37* (2006.01)
  *A61F 5/048* (2006.01)

(52) U.S. Cl.
  CPC .............. *A61F 5/3707* (2013.01); *A61F 5/048* (2013.01)

(58) Field of Classification Search
  CPC ......... A61H 1/0218; A61F 5/04; A61F 5/055; A61F 5/3707; A61F 5/05883; A61F 5/05891; A61F 5/5104
  USPC ............ 128/845, 869, 870, 873, 876; 602/13, 602/17–19, 32–36, 38, 60, 61, 74; 482/10, 482/11, 91, 92, 133–135, 139, 142–145, 482/148
  See application file for complete search history.

(56) References Cited

U.S. PATENT DOCUMENTS 1,082,043 A    12/1913  Payne et al.
1,390,301 A     9/1921  McManis et al.
(Continued)

FOREIGN PATENT DOCUMENTS

FR    1.108.031    1/1956
GB      862277     3/1961
(Continued)

OTHER PUBLICATIONS

Author Unknown, "Product Information relating to the XZ Traction Wall Unit, and the XZ Traction Wall Unit 3D Traction Wings," Circular Traction Supply, Inc., no date, 16 pages.
(Continued)

*Primary Examiner* — Kim Lewis
(74) *Attorney, Agent, or Firm* — Kilpatrick Townsend & Stockton LLP

(57) ABSTRACT

A cervical restraint, traction, and exercise device and method includes a padded restraint system for a person's head, and an adjustable support system. The head may be placed in any of a number of three dimensional orientations until a particular orientation is reached, for example a pain-free or substantially pain-free orientation, and then a restraint system engaged, restraining the head in the particular three dimensional orientation against a set of one or more pads. The system may then be adjusted to apply a traction force. The device may be used in conjunction with a second restraint system that positions and restrains the person's torso. Use of the system may enable the user to perform exercises while certain body parts, including the head and neck, are restrained in pain-free or substantially pain-free positions to obtain therapeutic effects.

19 Claims, 7 Drawing Sheets

(56) References Cited

U.S. PATENT DOCUMENTS

| | | | |
|---|---|---|---|
| 1,936,363 A | | 11/1933 | Murray |
| 2,102,069 A | | 12/1937 | Bond |
| 2,262,271 A | | 11/1941 | De Camp |
| 2,693,796 A | | 11/1954 | Warner |
| 2,722,929 A | | 11/1955 | Little |
| 2,786,512 A | | 3/1957 | Moyer |
| 2,941,526 A | | 6/1960 | Mott |
| 2,949,911 A | | 8/1960 | Kennard et al. |
| 2,999,496 A | | 9/1961 | Parson |
| 3,170,659 A | * | 2/1965 | Wood, Jr. ................. 244/122 B |
| 3,548,816 A | | 12/1970 | Hanicke |
| 3,554,189 A | | 1/1971 | Hendrickson |
| 3,596,655 A | * | 8/1971 | Corcoran ........................ 602/32 |
| 3,621,839 A | * | 11/1971 | Barthe ................. A61H 1/0218 |
| | | | 602/32 |
| 3,675,646 A | | 7/1972 | Corcoran |
| 3,685,511 A | | 8/1972 | Alvarez |
| 4,271,830 A | | 6/1981 | Moon |
| 4,354,485 A | * | 10/1982 | Safadago ..................... 606/242 |
| 4,372,552 A | | 2/1983 | Carlmark |
| 4,508,109 A | | 4/1985 | Saunders |
| 4,807,870 A | * | 2/1989 | Hickman ........................ 482/68 |
| 4,903,689 A | | 2/1990 | Lannertone |
| 5,042,800 A | | 8/1991 | Walter |
| 5,050,589 A | | 9/1991 | Engle |
| 5,074,000 A | | 12/1991 | Soltani et al. |
| 5,110,122 A | | 5/1992 | Moore et al. |
| 5,224,924 A | | 7/1993 | Urso |
| 5,334,123 A | | 8/1994 | Rutherford |
| 5,575,765 A | * | 11/1996 | Foster ............................. 602/32 |
| 5,713,841 A | * | 2/1998 | Graham ............... A61H 1/0218 |
| | | | 128/DIG. 20 |
| 5,800,366 A | | 9/1998 | Bertrand |
| 5,840,001 A | | 11/1998 | Schedel |
| 5,885,197 A | | 3/1999 | Barton |
| 5,940,911 A | | 8/1999 | Wang |
| 5,967,956 A | | 10/1999 | Teeter |
| 6,106,445 A | * | 8/2000 | Lay ...................... A61H 1/0296 |
| | | | 482/142 |
| 6,243,897 B1 | | 6/2001 | Sumiya |
| 6,416,447 B1 | | 7/2002 | Harmon |
| 6,428,033 B1 | | 8/2002 | Harrison et al. |
| 6,428,497 B1 | | 8/2002 | Crouch |
| 6,435,611 B1 | | 8/2002 | Walter |
| 6,565,112 B2 | | 5/2003 | Hanson et al. |
| 6,637,055 B1 | | 10/2003 | Nanan |
| 6,656,098 B2 | | 12/2003 | Hoffman |
| 6,681,770 B1 | | 1/2004 | Dreher |
| 6,692,451 B2 | | 2/2004 | Splane, Jr. |
| 6,749,548 B2 | | 6/2004 | Hoffman |
| 6,811,522 B1 | | 11/2004 | McQuinn |
| 6,821,288 B2 | | 11/2004 | Schaeffer |
| 6,971,997 B1 | | 12/2005 | Ryan et al. |
| 7,052,448 B2 | | 5/2006 | Teeter |
| 7,081,073 B1 | | 7/2006 | Smith |
| 7,288,050 B2 | | 10/2007 | Murphy |
| 7,294,094 B1 | | 11/2007 | Howle |
| 7,357,777 B1 | | 4/2008 | Meyers |
| 7,361,128 B2 | | 4/2008 | Chen |
| 7,534,213 B2 | | 5/2009 | Shelbourne et al. |
| 8,001,970 B2 | * | 8/2011 | King et al. ................... 128/845 |
| 8,021,287 B2 | | 9/2011 | Hoffman et al. |
| 2002/0084627 A1 | | 7/2002 | Harrison et al. |
| 2004/0073150 A1 | | 4/2004 | Roballey |
| 2005/0209055 A1 | | 9/2005 | Anders |
| 2006/0003877 A1 | | 1/2006 | Harmon |
| 2006/0190010 A1 | | 8/2006 | Easton |
| 2006/0197314 A1 | | 9/2006 | Harrison et al. |
| 2007/0038162 A1 | | 2/2007 | Alexiadis |
| 2007/0087921 A1 | | 4/2007 | Graham |
| 2007/0161477 A1 | | 7/2007 | Wang |
| 2008/0176716 A1 | | 7/2008 | Boren |
| 2008/0227610 A1 | | 9/2008 | Chen |
| 2008/0269030 A1 | | 10/2008 | Hoffman et al. |
| 2012/0265114 A1 | * | 10/2012 | Kang ..................... A61F 5/042 |
| | | | 602/35 |

FOREIGN PATENT DOCUMENTS

| | | |
|---|---|---|
| JP | 2001-212163 A | 8/2001 |
| KR | 20-0277064 | 6/2002 |
| RU | 2014042 C1 * | 6/1994 |
| WO | 98/15251 | 4/1998 |

OTHER PUBLICATIONS

Author Unknown, "Chapter 5, History of Lumbar Traction," Harrison CBP Seminars, Inc., 2004, 19 pages.

European Search Report of EP 08153471 mailed on Aug. 8, 2008, 6 pages.

Foster, S., "Full Spine Postural Traction in the Five Point Traction System," Sep. 1998, 7 pages.

Harrison, D., et al., "The Lumber Spine, Structural Assessment and Rehabilitation: The Chiropractic Biophysics® (CPB®) Approach," 1998, 11 pages.

Korean Intellectual Property Office, Final Rejection of Application No. 10-2008-0022886 dated Jan. 28, 2011, 4 pages.

Korean Intellectual Property Office, Non-Final Rejection of Application No. 10-2008-0022886 dated Nov. 26, 2007, 4 pages.

Oakley, P., et al., "A History of Spine Traction," Journal of Vertebral Subluxation Research, Mar. 2, 2007, 12 pages.

International Search Report and Written Opinion of PCT/US2012/037451 mailed on Aug. 24, 2012, 10 pages.

International Preliminary Report on Patentability for PCT/US2012/037451 mailed Nov. 21, 2013, 7 pages.

* cited by examiner

CERVICAL REPOSITIONING, RESTRAINT, TRACTION AND EXERCISE DEVICE AND METHOD

This application claims priority to provisional U.S. Patent Application No. 61/484,802 filed May 11, 2011 and titled "Cervical Repositioning, Restraint, Traction and Exercise Device", the entire disclosure of which is hereby incorporated by reference herein for all purposes.

BACKGROUND

Many people throughout the world suffer from chronic back and neck pain. The causes of back and neck pain are too numerous to enumerate, but include injuries, bad posture, accidents, genetic defects, disease, and aging. For some, the pain arises only during exercise. As a result, many eliminate beneficial exercises from their routines. For others, neck, hip and/or lower back pain is always present. Exercise may be a desirable or a necessary treatment for the pain for many of these people. But again, the very exercises needed to alleviate the pain are difficult to perform due to the increased pain during exercise. These people often become stuck in a cycle of increasing pain as the exercises and treatments needed to alleviate pain are too painful to perform, with the lack of proper exercise resulting in weakening of the muscles and increased pain and/or discomfort.

BRIEF SUMMARY

In one aspect, a cervical restraint, traction, and exercise device includes one or more pads shaped and positioned to engage a head of a person, an adjustable support system to which the one or more pads are mounted, and a restraint system for restraining the head. When the restraint system is disengaged, the head is positionable in any number of three-dimensional orientations in relation to the one or more pads, and when the restraint system is engaged, the head is restrained in a particular three-dimensional orientation against the pads. The adjustable support system is movable to apply spinal traction between the head and a torso of the person. In some embodiments, the restraint system is a first restraint system, and the device further includes a second restraint system shaped and positioned to receive and restrain the torso of the person. In some embodiments, the device has a front, a back, a top, a bottom, and left and right sides, and the adjustable support system can be adjusted in any one, any combination, or all of left and right, front and back, and up and down to reach the particular three-dimensional orientation of the person's head. The one or more pads may include multiple pads, and the adjustable support system may enable independent adjustment of each pad in relation to the other pads in at least one direction of motion. In some embodiments, when the first restraint system is disengaged, the head of the person can be moved in any one, any combination, or all of roll, pitch, and yaw, to reach the particular three-dimensional orientation. In some embodiments, the adjustable support system includes a left track; left inner and left outer brackets that are independently slidable within the left track, each of the left inner and left outer brackets holding one respective pad; a right track; and right inner and right outer brackets that are independently slidable within the right track, each of the right inner and right outer brackets holding one respective pad. The left and right tracks may be independently movable to raise and lower the pads. The restraint system may include one or more lower pads configured to fit under the lower portion of the head and jaw of the user. In some embodiments, the restraint system further includes a set of adjustable length tethers that couple the one or more lower pads to the support structure. The one or more lower pads may include only a single U- or horseshoe-shaped pad. In some embodiments, the device can apply unilateral traction. In some embodiments, the second restraint system includes a padded torso support, and one or more adjustable torso restraints to restrain the torso of the person to the padded torso support.

According to another aspect, a method includes engaging a head of a person with an adjustable support system that includes at least one pad shaped to conform to the head of the person, positioning the head in any of a number of three dimensional orientations until a particular three dimensional orientation is reached, restraining the head in the particular three dimensional orientation within the adjustable support system, and mechanically applying spinal traction between the head and torso. Positioning the head in any of a number of three dimensional orientations until a particular three dimensional orientation is reached may include positioning the head in any of a number of three dimensional orientations until the user reports that a pain free or substantially pain free three dimensional orientation has been reached. In some embodiments, the method further includes restraining the torso of the person. Restraining the torso of the person may include restraining the torso of the person in a pain free or substantially pain free position as determined by the person. In some embodiments, restraining the head in the particular three dimensional orientation includes engaging a lower pad under the lower portion of the head and jaw of the person, and coupling the lower pad to the adjustable support system to hold the head against the adjustable support system. The person may perform exercise while the head and torso of the person are restrained. In some embodiments, the particular three dimensional orientation is a first particular three dimensional orientation, and the method further includes releasing the head of the person, repositioning the head in any of a number of three dimensional orientations until a second particular three dimensional orientation is reached, and restraining the head in the second particular three dimensional orientation within the adjustable support system.

According to another aspect, a method includes engaging a head of a person with an adjustable support system that includes at least one pad shaped to conform to the head of the person, positioning the head in any of a number of three dimensional orientations until a particular three dimensional orientation is reached, restraining the head in the particular three dimensional orientation within the adjustable support system, restraining the torso of the person in a particular three-dimensional torso orientation, and the user performing exercise while the user's head and torso are restrained. The method may further include adjusting the adjustable support system to apply spinal traction to the person between the head and torso of the person. Positioning the head in any of a number of three dimensional orientations until a particular three dimensional orientation is reached may include positioning the head in any of a number of three dimensional orientations until the user reports that a pain free or substantially pain free three dimensional orientation has been reached.

DETAILED DESCRIPTION

Figure 1:
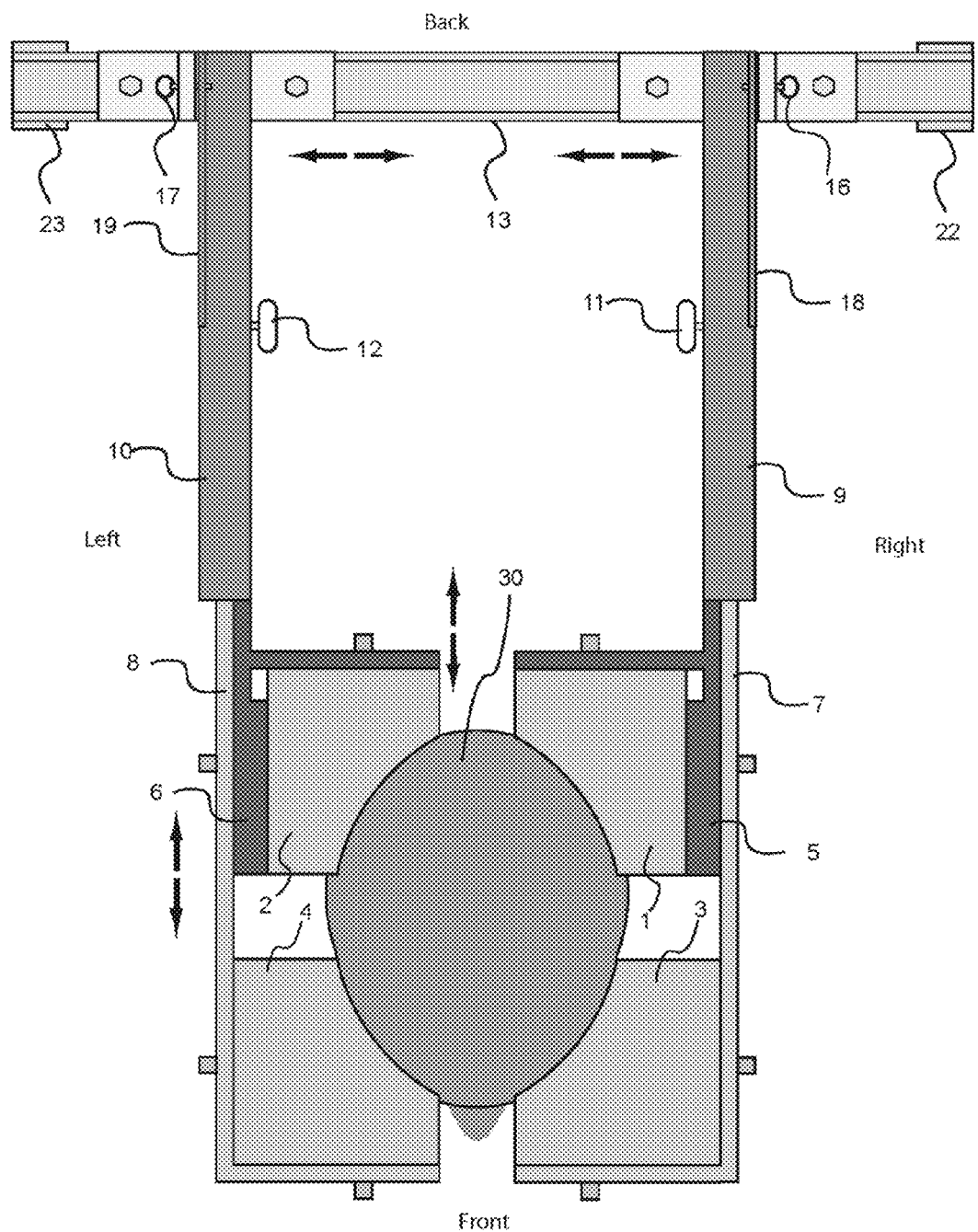
FIG. 1 shows a top plan view of a first embodiment of a cervical restraint, traction, and exercise device constructed according to principles of the invention.
Figure 2:
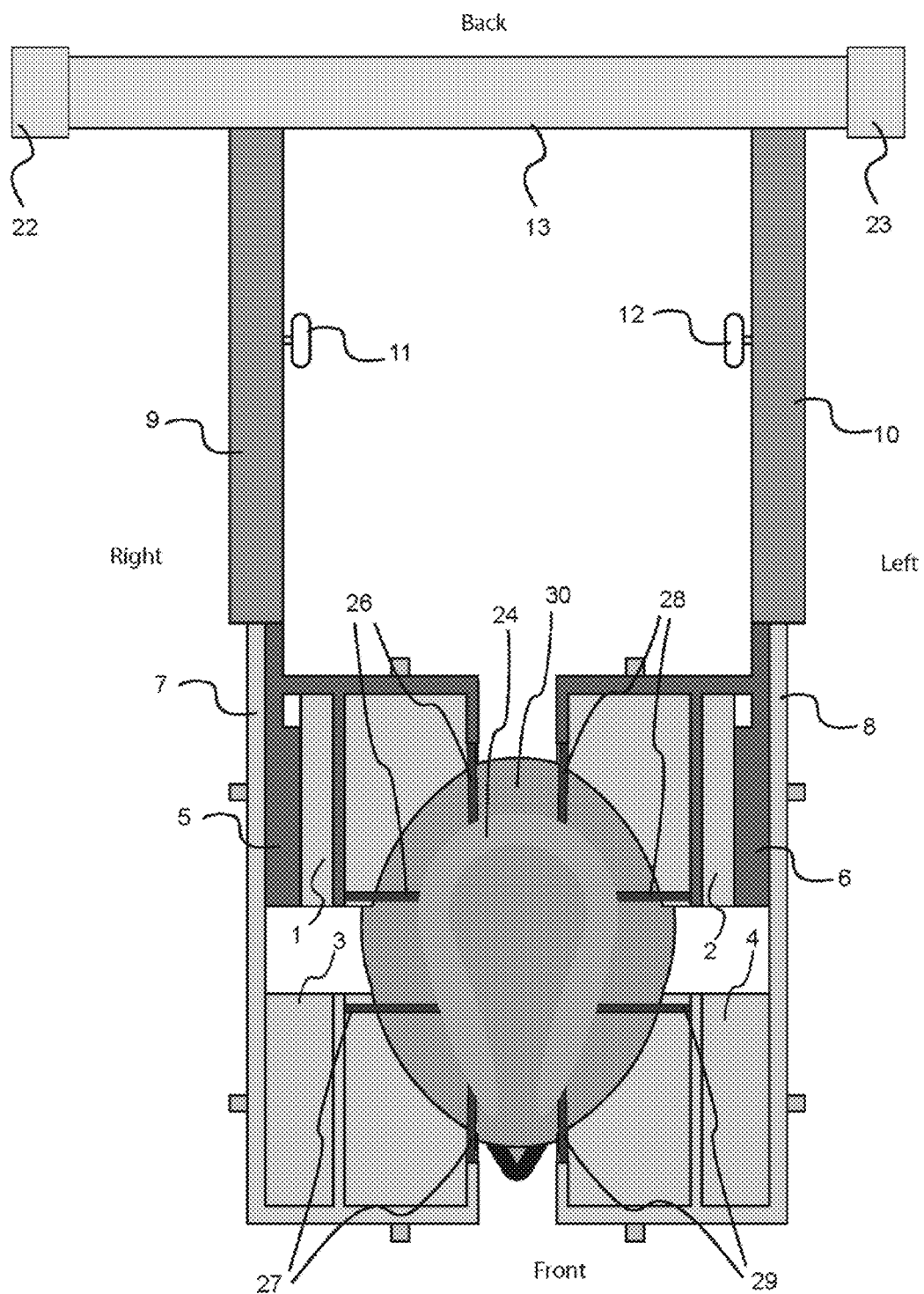
FIG. 2 shows a bottom plan view of the device of FIG. 1.

FIG. 1 shows a top plan view of a first embodiment of a cervical restraint, traction, and exercise device constructed according to principles of the invention. The top of head 30 of a person is visible in the FIG. 1, facing the front of the device. Left and right sides, a front, and a back of the device are labeled in FIG. 1. The device also has a top and a bottom. It will be recognized that in this context, the sides, front, back, top, and bottom are defined for the purposes of establishing a coordinate system for the device, and do not refer to particular physical elements of the device. In the figures, "left" and "right" are defined from the point of view of a person viewing the device from the front, and not from the point of view of the person using the device.

A set of upper pads includes pads 1, 2, 3, and 4, which are shaped and positioned engage the user's head 30. For example, pads 1-4 may be generally rectangular with a rounded cutout on one corner of each pad so that each pad fits comfortably at any point around the head 30. Pads 1-4 may be made of a compliant foam or other material covered by an outer shell, for example leather or a natural or synthetic fabric. Pads 1-4 are mounted to an adjustable support system that includes several components. For example, pad 1 is attached to a right inner bracket 5, and pad 3 is attached to a right outer bracket 7. Similarly, pad 2 is attached to a left inner bracket 6, and pad 4 is attached to a left outer bracket 8. Brackets 5 and 7 slide into a right track 9, such that they can slide independently of each other within track 9. A bolt, knob, or other suitable device 11 is threaded into track 9, and when tightened, clamps brackets 5 and 7 in position in relation to track 9, thus fixing the front-to-back positions of pads 1 and 3. A similar construction may be provided on the left side, where brackets 6 and 8 slide independently in left track 10, and can be clamped in place using bolt, knob, or other device 12 to fix the front-to-back positions of pads 2 and 4. Any suitable means may be used to form the sliding and clamping arrangement. For example, alternative clamping means include, setscrews, detent mechanisms, or other kinds of mechanisms or combinations of mechanisms. Alternative sliding mechanisms may use guide rods with pillow blocks, leadscrews, or other kinds of mechanisms or combinations of mechanisms. The components of the support system are preferably made of a strong, durable material such as steel, although other materials may be used in some embodiments, such as aluminum, plastics, composites, or combinations including any of these materials.

Each of tracks 9 and 10 may be both slidingly and pivotally attached to crossbeam 13. In the sliding attachment, each of tracks 9 and 10 can slide independently left or right, i.e. along the axial length of crossbeam 13, to adjust the left-to-right positions of pads 1 and 3, and pads 2 and 4, respectively. Any means known in the art may be used to form the sliding attachment. For example, crossbeam 13 may include a generally U-shaped channel and mounts for tracks 9 and 10 may slide within the channel. Any mechanical support structure can be employed, so long as the head 30 can be nested within the pads and adjusted. For example, the head may be positioned forwards and backwards, left and right, and at any angle of rotation. After adjustment, the positions of tracks 9 and 10 with respect to crossbeam 13 may be locked, if desired, using any suitable mechanism, such as clamps, setscrews, detent mechanisms, or another kind of locking mechanism.

Figure 4:
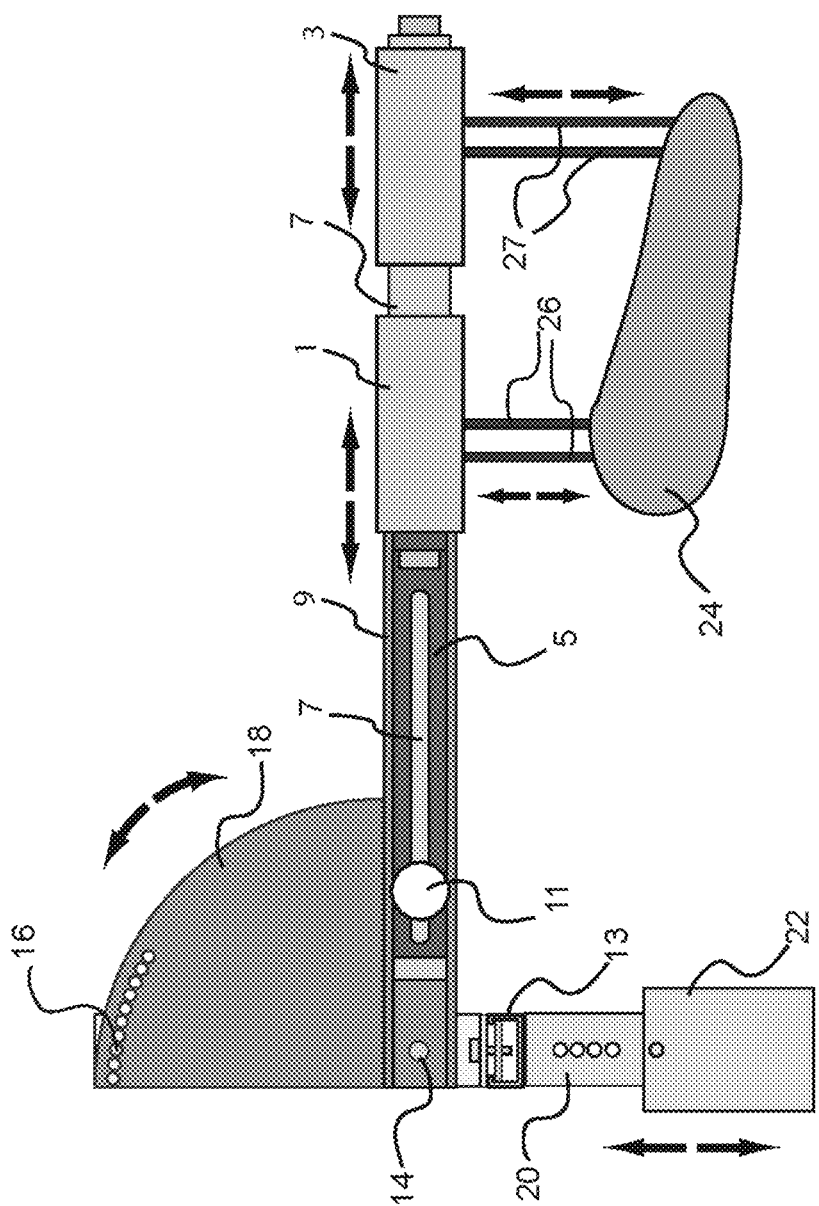
FIG. 4 shows a left side elevational view from the interior of the device of FIG. 1.
Figure 5:
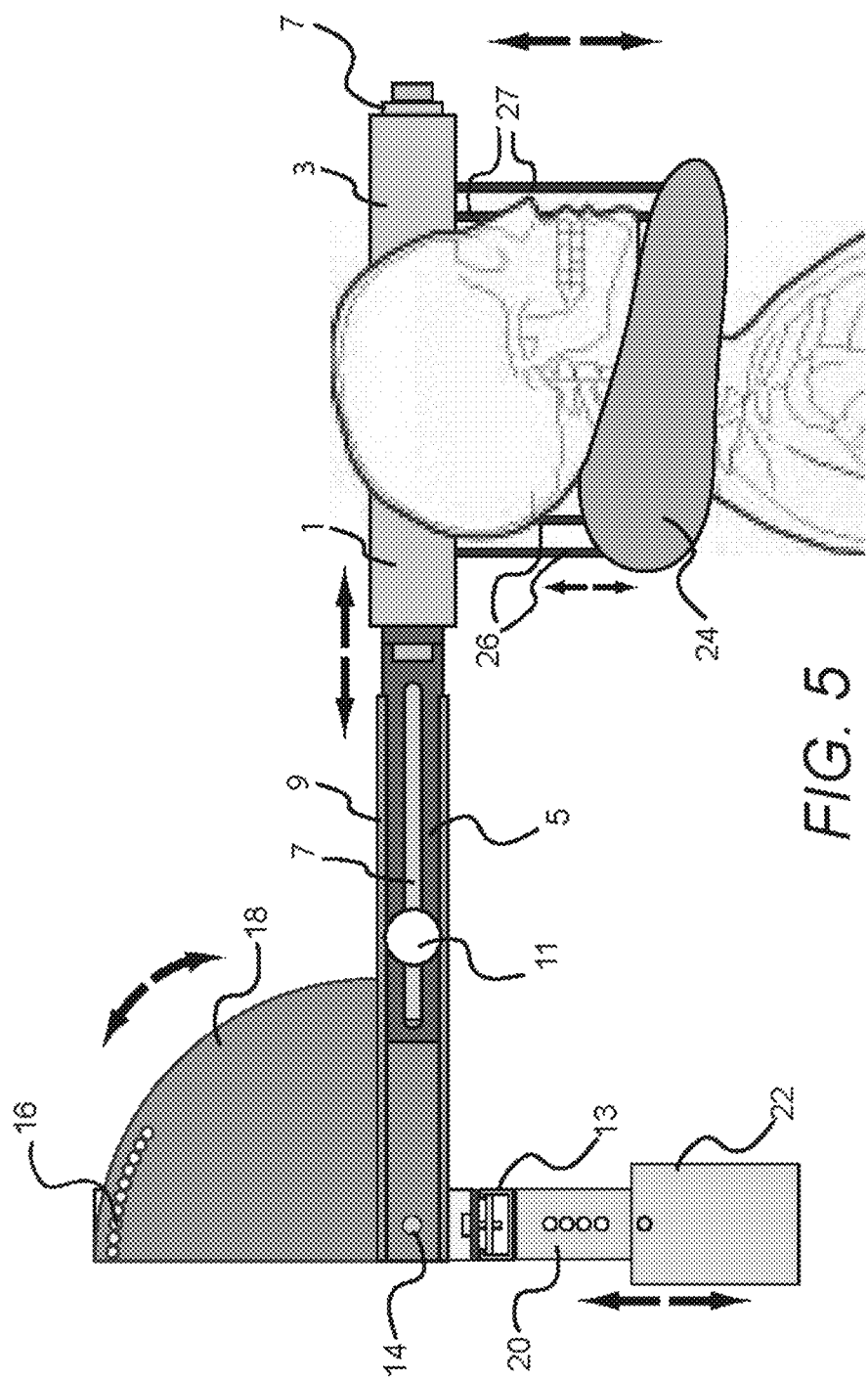
FIG. 5 shows the device of FIG. 1 in a view similar to that of FIG. 4, engaged with a head of a person.
Figure 6:
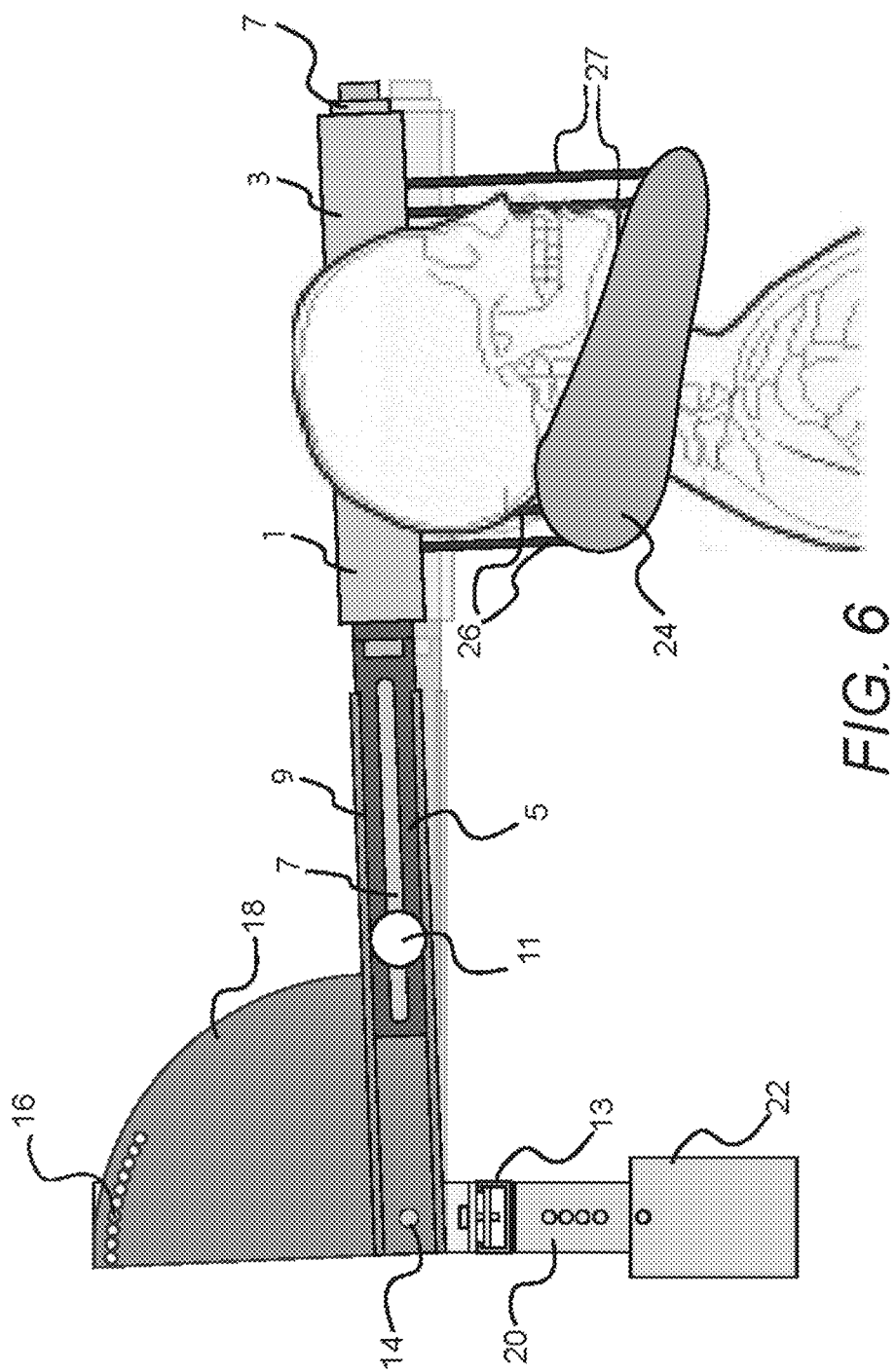
FIG. 6 shows the device of FIG. 1 in a view similar to that of FIG. 5, with a portion of a support system raised to apply a traction force to the person.

As is best seen in FIGS. 4-6, track 9 is also pivotable with respect to crossbeam 13, about pin 14. Similarly, track 10 on the left side of the device is pivotable with respect to crossbeam 13, about pin 15. Any means known in the art may be employed to form the pivotable connections, such as those described below or other means. The pivotal connections may be used to adjust the system to the height of a particular patient, or to provide a traction force as is explained in more detail below. In other embodiments, tracks 9 and 10 may be translatable vertically with respect to crossbar 13, instead of or in addition to being pivotable, so that vertical adjustment can be accomplished by moving tracks 9 and 10 in a vertical direction. when tracks 9 and 10 may be both rotatable with respect to crossbar 13 and vertically translatable with respect to crossbar, vertical adjustment can be accomplished by either or both of rotation and vertical translation of tracks 9 and 10. Tracks 9 and 10 are preferably movable independently of each other, whether in rotation, translation or both. In addition to vertical adjustment, motions of tracks 9 and 10 may be used for applying traction force.

Referring to FIG. 4, a right plate 18 is fixed to right track 9, for example by welding, and includes a set of transverse holes arranged at a constant radial distance from pin 14. As track 9 is rotated, a right spring-loaded locking pin 16 can be released into any of the holes to fix the angle of track 9 with respect to crossbeam 13. Track 9 can thus be locked at any of a plurality of angles with respect to crossbeam 13.

Figure 3:
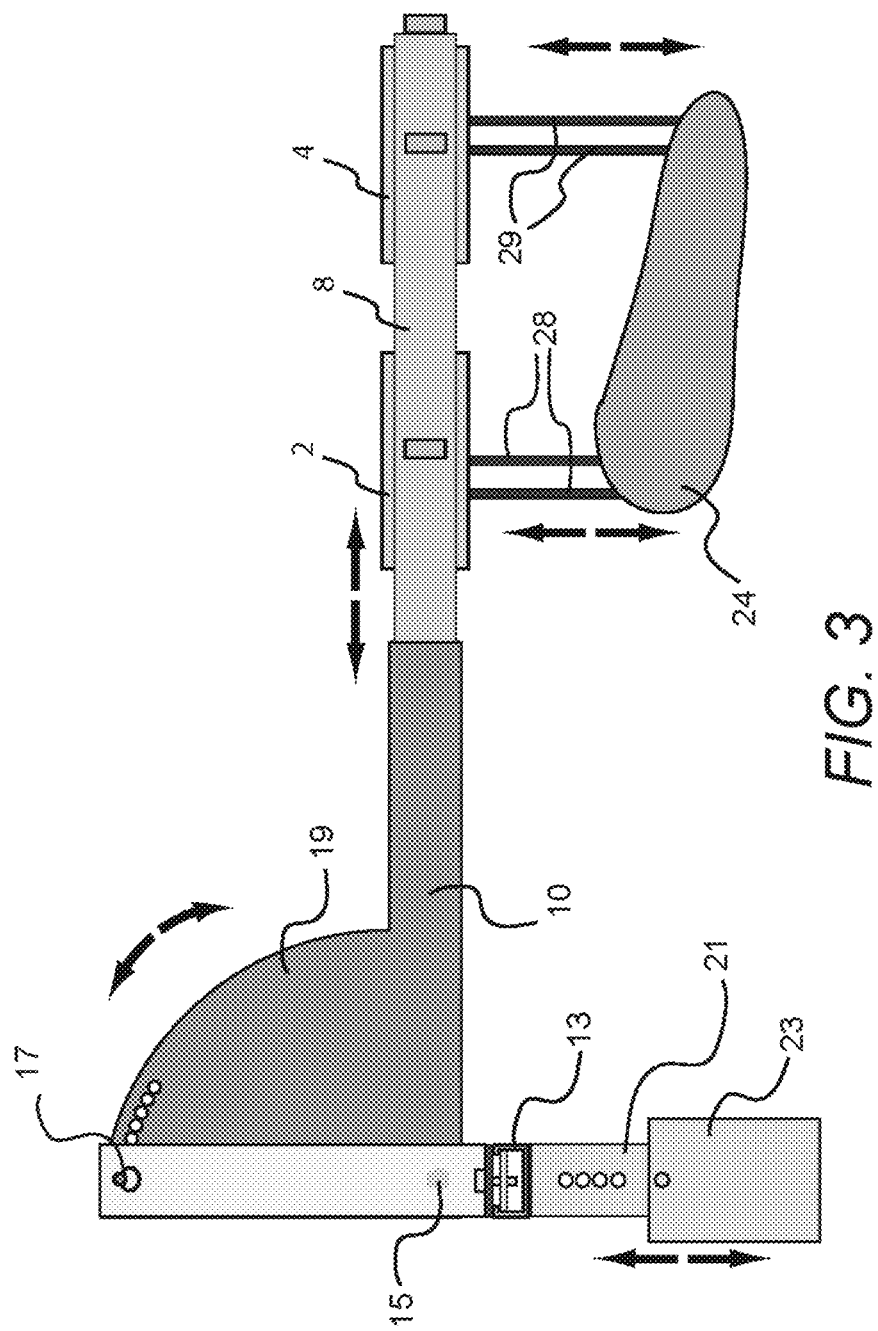
FIG. 3 shows a left side elevational view of the device of FIG. 1.

Referring to FIG. 3, a similar left plate 19 is fixed to left track 10, and includes a set of transverse holes arranged at a constant radial distance from pin 15. As track 10 is rotated, a left spring-loaded locking pin 17 can be released into any of the holes in plate 19 to lock track 10 at any of a plurality of heights. Any suitable mechanism for locking the positions of plates 18 and 19 may be used, and alternatives to pins 15 and 16 include clamps, setscrews, detent mechanisms, and other kinds of mechanisms.

Crossbeam 13 may also be adjustable up and down in the vertical direction, transverse to the axial length of crossbeam 13. This adjustment may also be used to adjust the system to the height of a particular user, or to apply traction force. Any suitable connection may be used to achieve the vertical adjustment, such as that described below. As is best seen in FIGS. 3 and 4, the right end of crossbeam 13 may be attached to a right sliding post 20, and the left end of crossbeam 13 attached to a left sliding post 21. Right sliding post 20 can slide up and down within right vertical channel 22, and can be pinned at any of a number of vertical positions by a pin through right vertical channel 22 and any of a set of holes in right sliding post 20. Similarly, left sliding post 21 can slide up and down within left vertical channel 23, and can be pinned in place. The height of crossbeam 13 can thus be adjusted and crossbeam 13 can be fixed at any of a number of heights. Adjusting the height of crossbeam 13 adjusts the height of the entire support structure as a unit. In some embodiments, the two ends of crossbeam 13 may be raised and lowered independently. This capability provides for additional adjustability, and may assist in applying unilateral traction on one side of the person. Alternatively or in addition, the attachment points of tracks 9 and 10 could be movable vertically, so that tracks 9 and 10 can be independently moved up and down to achieve the additional adjustability and unilateral traction capability.

A lower pad 24 may be U- or horseshoe-shaped and is configured to fit under the lower portion of the head and jaw of the user. Lower pad 24 is coupled to the support structure by a restraint system, which may take any form, so long as it can restrain the user's head in a selected position against pads 1-4. While only a single lower pad 24 is shown, lower pad 24 may include multiple pad segments. In the example embodiment shown, the restraint system includes four adjustable length tethers 26, 27, 28, and 29. Tether 26 attaches to lower pad 24 at a right rear location and couples it to the support structure. Tether 27 attaches to lower pad 24 at a right front location and couples it to the support structure. Tether 28 attaches to lower pad 24 at a left rear location and couples it to the support structure. Tether 29 attaches to lower pad 24 at a left front location and couples it to the support structure. When the tethers are relaxed, head 30 of the user is free to be positioned in any number of three dimensional orientations until a particular three dimensional orientation is reached, such as a substantially pain-free orientation. For example, the user may adjust the system forward and backward, left and right, and up and down, and may move and rotate head 30 in any axis of rotation until an orientation is reached in which the user does not feel any or significant neck pain. Rotation may include pitch (forward or backward motion similar to nodding of the head), roll (turning the head side to side), yaw (rocking the head toward or away from a shoulder), or any combination of these. Tethers 26-29 may then be shortened, engaging the restraint system and restraining head 30 against pads 1-4 in the selected position. More or fewer tethers may be used in other embodiments, and the tension in the tethers may be adjusted as a means of adjusting a traction force applied by the system. For the purposes of this disclosure, a substantially pain free orientation is one in which the user's level of pain is low enough to permit the user to perform exercise.

In some embodiments, a traction force is applied between the user's head and torso. For example, after restraining the user's head 30 in the restraint system, the adjustable support system may be adjusted upward to apply the traction force. The traction force may be resisted simply by the user's weight, but in some embodiments, the person's torso may also be restrained to resist the traction force. For example, the illustrated cervical restraint, fraction, and exercise device may be mounted to another device such as those described in U.S. Pat. No. 6,749,548, titled "Restraint and Exercise Device" and issued to Hoffman on Jun. 15, 2004, and U.S. Pat. No. 8,021,287, titled "Restraint, Reposition, Traction and Exercise Device and Method" and issued to Hoffman et al. on Aug. 31, 2011, the disclosures of which are hereby incorporated by reference herein in their entirety.

Figure 7:
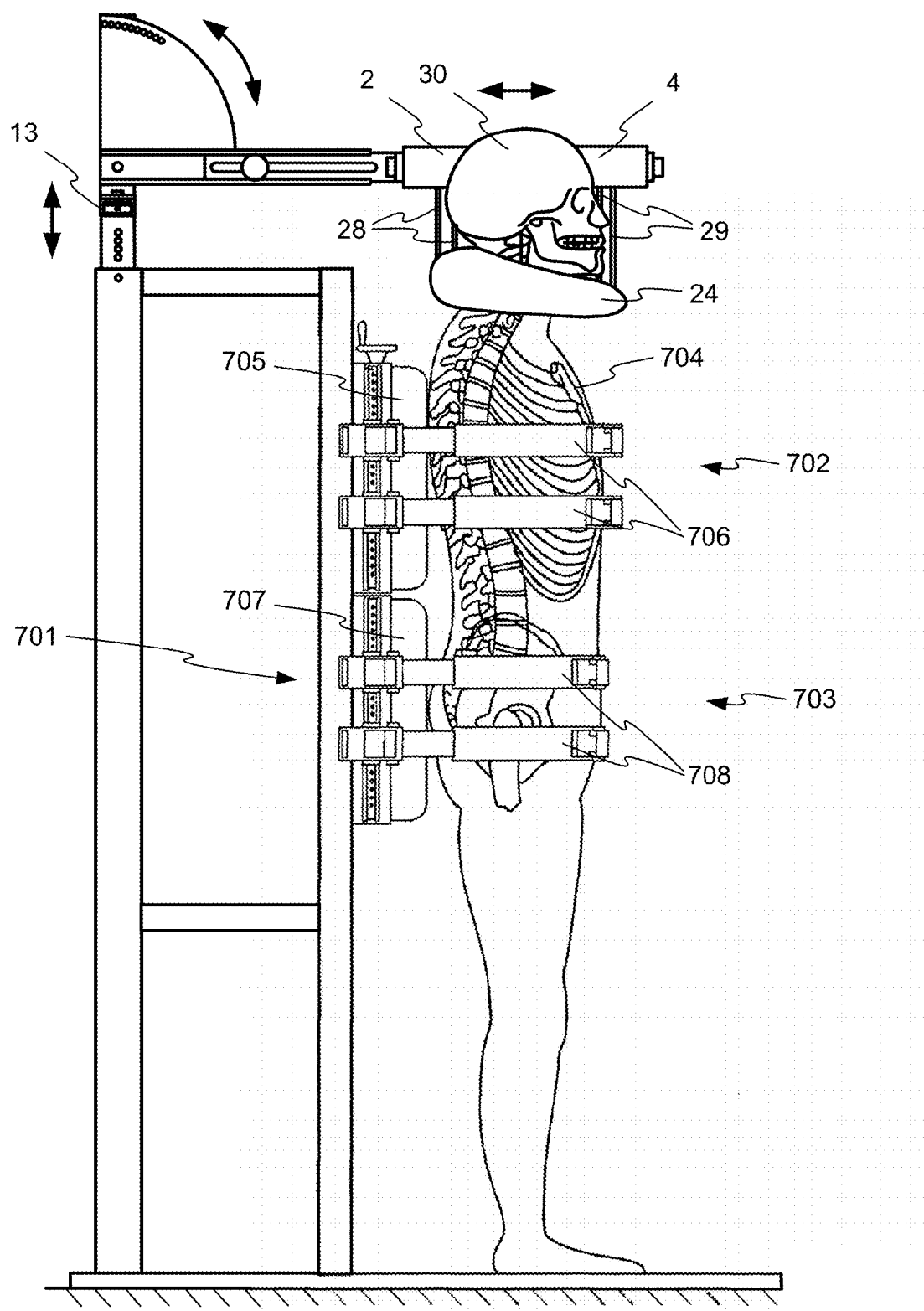
FIG. 7 shows the device of FIG. 1 integrated with another device for restraining the user's torso.

FIG. 7 illustrates the device of FIGS. 1-4 integrated with another device 701 for restraining the torso 702 and pelvic area 703 of a user 704 in accordance with embodiments of the invention. Although other devices may be envisioned, device 701 may be, for example, similar to any of the devices shown in U.S. Pat. Nos. 6,749,548 and 8,021,287 previously incorporated by reference, and more information about some possible devices 701 may be found in those patents. In this example, torso 702 is restrained against padded torso support 705 by one or more torso restraints 706. Torso restraints 706 may conveniently be straps with ratcheting mechanisms for adjusting the tension in the straps, but other kinds of restraints may be used. The user may position himself or herself against padded torso support 705 in any workable position, for example a pain free or substantially pain free position, before torso restraints 706 are tightened to restrain torso 702. While the example of FIG. 7 shows the user's back against padded torso support 705, any workable position may be used. For example, the user may face padded torso support 705, or place either side against padded torso support 705. Similarly, in some embodiments the user's pelvic area 703 may be restrained against a padded pelvic support 707, using one or more pelvic restraints 708. The user may position himself or herself against padded pelvic support 707 in any workable position, for example a pain free or substantially pain free position before pelvic restraints 708 are tightened to restrain pelvic area 703. One of both of padded torso support 705 and padded pelvic support 707 may be adjustable to adapt the system to the height of a particular user 704. In some embodiments, one or both of padded torso support 705 and padded pelvic support 707 may be movable to provide spinal traction to a part of the user's body between the two supports. Padded torso support 705 may be split, so that two sides of padded torso support 705 are movable independently.

In combination with restraining the user's torso 702, the system of FIG. 7 enables restraint of the user's head 30. In this example, head 30 is shown as engaged with pads 2 and 4, while pads 1 and 3 are not shown for clarity of illustration. The adjustable support system enables adjustment of the locations of pads 1-4 forward, backward, side to side, and up and down as needed to reach a particular position of head 30. Lower pad 24 is positioned under the lower portion of the head and jaw of the user, and suspended by adjustable tethers including tethers 28 and 29. (Tethers 26 and 27 are not shown in FIG. 7.) Adjustable tethers 26-29 can then be tightened to restrain head 30 against pads 1-4. Once head 30 is restrained, the user may perform exercises, or may simply enjoy pain relief that results from the external immobilization of portions of his or her body. If desired, the restraint system may be released and head 30 repositioned to a second three dimensional orientation, and then the restraint system may be reengaged to restrain head 30 in the second three dimensional orientation.

When a traction force is desired, the traction force may be applied in any of several ways. For example, either or both of tracks 9 and 10 may be pivoted about their respective axes or otherwise moved to raise either or both sides of lower pad 24, thus pulling pad 24 against the user's lower jaw and head, and exerting a traction force. When only right track 9 is raised, the right side of lower pad 24 is raised, and the system creates a unilateral traction force on the person's left side. Similarly, when left track 10 is raised, the left side of lower pad 24 is raised, and the system creates a unilateral traction force on the person's right side. When both tracks 9 and 10 are raised, by equal or different amounts, then a general traction force is created. Alternatively or additionally, the entire support system can be raised as a unit by raising crossbeam 13 and pinning sliding posts 20 and 21 in a specific vertical position that exerts a traction force on the user.

Tethers 26-29 may also be adjusted to configure traction forces. For example, by reducing the lengths of rear tethers 26 and 28 in relation to the lengths of front tethers 27 and 29, a posterior traction force is achieved. Similarly, when the lengths of front tethers 27 and 29 are reduced in relation to the lengths of rear tethers 26 and 29, an anterior (frontal) traction force is created. The system provides fully independent control over the sections of lower pad 24, and traction forces can be achieved in an infinite number of angles and directions.

Use of embodiments of the invention may provide significant benefits. For example, a user may position himself or herself in a substantially or completely pain-free orientation, and perform exercises while certain body parts, including the neck and head, are restrained to remain in the pain-free orientation. The user may be in a functional, weight-bearing upright position. Use of the system may enable the user to participate in exercise, with its attendant health benefits, which may have otherwise been painful. The pain relief may be long-lasting, particularly if the system of the invention is used in a regular exercise routine.

While particular embodiments have been described, many variations are possible within the scope of the appended claims. For example, when torso support is used, any suitable device or arrangement may be used to provide it. It is to be understood that any workable subset or combination of the features disclosed is also considered to be disclosed.

What is claimed is:

1. A cervical restraint, traction, and exercise device, comprising:
   one or more upper pads shaped and positioned to engage an upper portion of a head of a person;
   an adjustable support system to which the one or more upper pads are mounted; and
   a restraint system for restraining the head, wherein when the restraint system is disengaged, the head is positionable in any number of three-dimensional orientations in relation to the one or more upper pads, and when the restraint system is engaged, the head is restrained in a particular three-dimensional orientation against the one or more upper pads;
   wherein the restraint system comprises one or more lower pads configured to fit under the lower portion of the back of the head and jaw of the user, and the restraint system is configured to exert upward force on the head using the one or more lower pads to restrain and immobilize the head upwardly against the one or more upper pads; and
   wherein the adjustable support system is movable to apply spinal traction between the head and a torso of the person.

2. The cervical restraint, traction, and exercise device of claim 1, wherein the restraint system is a first restraint system, the device further comprising a second restraint system shaped and positioned to receive and restrain the torso of the person.

3. The cervical restraint, traction, and exercise device of claim 2, wherein the device has a front, a back, a top, a bottom, and left and right sides, and wherein the adjustable support system can be adjusted in any one, any combination, or all of left and right, front and back, and up and down to reach the particular three-dimensional orientation of the person's head.

4. The cervical restraint, traction, and exercise device of claim 3, wherein the one or more upper pads comprise multiple upper pads, and wherein the adjustable support system enables independent adjustment of each upper pad in relation to the other upper pads in at least one direction of motion.

5. The cervical restraint, traction, and exercise device of claim 3, wherein when the first restraint system is disengaged, the head of the person can be moved in any one, any combination, or all of roll, pitch, and yaw, to reach the particular three-dimensional orientation.

6. The cervical restraint, traction, and exercise device of claim 5, wherein the device can apply unilateral traction.

7. The cervical restraint, traction, and exercise device of claim 5, wherein the second restraint system comprises:
   a padded torso support; and
   one or more adjustable torso restraints to restrain the torso of the person to the padded torso support.

8. The cervical restraint, traction, and exercise device of claim 1, wherein the restraint system further comprises a set of adjustable length tethers that couple the one or more lower pads to the support structure.

9. The cervical restraint, traction, and exercise device of claim 1, wherein the one or more lower pads include only a single U- or horseshoe-shaped pad.

10. A cervical restraint, traction, and exercise device, comprising:
    one or more pads shaped and positioned to engage a head of a person;
    an adjustable support system to which the one or more pads are mounted;
    a first restraint system for restraining the head, wherein when the restraint system is disengaged, the head is positionable in any number of three-dimensional orientations in relation to the one or more pads, and when the restraint system is engaged, the head is restrained in a particular three-dimensional orientation against the one or more pads; and
    a second restraint system shaped and positioned to receive and restrain the torso of the person;
    wherein the adjustable support system comprises:
    a left track;
    left inner and left outer brackets that are independently slidable within the left track, each of the left inner and left outer brackets holding one respective pad;
    a right track; and
    right inner and right outer brackets that are independently slidable within the right track, each of the right inner and right outer brackets holding one respective pad;
    wherein the device has a front, a back, a top, a bottom, and left and right sides, and wherein the adjustable support system can be adjusted in any one, any combination, or all of left and right, front and back, and up and down to reach the particular three-dimensional orientation of the person's head;
    wherein when the first restraint system is disengaged, the head of the person can be moved in any one, any combination, or all of roll, pitch, and yaw, to reach the particular three-dimensional orientation; and
    wherein the adjustable support system is movable to apply spinal traction between the head and a torso of the person.

11. The cervical restraint, traction, and exercise device of claim 10, wherein the left and right tracks are independently movable to raise and lower the one or more pads.

12. A method of applying restraint and traction, comprising:
    engaging a head of a person with an adjustable support system that includes at least one upper pad shaped to conform to the upper portion of the head of the person;
    positioning the head in any of a number of three dimensional orientations until a particular three dimensional orientation is reached;
    restraining the head in the particular three dimensional orientation within the adjustable support system, wherein restraining the head in the particular three dimensional orientation comprises engaging a lower pad under the lower portion of the back of the head and jaw of the person and coupling the lower pad to the adjustable support system to hold the head upward against the at least one upper pad [shaped to conform to the upper portion of the head of the person]; and
    mechanically applying spinal traction between the head and torso.

13. The method of claim 12, wherein positioning the head in any of a number of three dimensional orientations until a particular three dimensional orientation is reached comprises positioning the head in any of a number of three dimensional orientations until the user reports that a pain free or substantially pain free three dimensional orientation has been reached.

14. The method of claim 12, further comprising restraining the torso of the person.

15. The method of claim 14, wherein restraining the torso of the person comprises restraining the torso of the person in a pain free or substantially pain free position as determined by the person.

16. The method of claim 12, further comprising the person performing exercise while the head and torso of the person are restrained.

17. The method of claim 12, wherein the particular three dimensional orientation is a first particular three dimensional orientation, the method further comprising:
    releasing the head of the person;
    repositioning the head in any of a number of three dimensional orientations until a second particular three dimensional orientation is reached; and
    restraining the head in the second particular three dimensional orientation within the adjustable support system.

18. A method of restraint and exercise, comprising:
    engaging a head of a person with an adjustable support system that includes at least one upper pad shaped to conform to an upper portion of the head of the person;
    positioning the head in any of a number of three dimensional orientations until a the person reports that a pain free or substantially pain free three dimensional orientation is reached;
    restraining the head in the pain free or substantially pain free three dimensional orientation within the adjustable support system, wherein restraining the head in the pain free or substantially pain free three dimensional orientation comprises engaging a lower pad under the lower portion of the back of the head and jaw of the person and coupling the lower pad to the adjustable support system to hold the head upward against the at least one upper pad;
    restraining the torso of the person in a particular three-dimensional torso orientation; and
    the person performing exercise while the person's head and torso are restrained.

19. The method of claim 18, further comprising adjusting the adjustable support system to apply spinal traction to the person between the head and torso of the person.

* * * * *